United States Patent [19]

Cavazza

[11] Patent Number: 4,743,621

[45] Date of Patent: May 10, 1988

[54] ESTER OF ACETYL CARNITINE, PROCESSES FOR ITS PREPARATION AND PHARMACEUTICAL COMPOSITIONS CONTAINING IT

[75] Inventor: Claudio Cavazza, Rome, Italy

[73] Assignee: SIGMA-TAU Industrie Farmaceutiche Riunite S.p.A., Rome, Italy

[21] Appl. No.: 746,731

[22] Filed: Jun. 20, 1985

[30] Foreign Application Priority Data

Jul. 4, 1984 [IT] Italy ............................ 48503 A/84

[51] Int. Cl.$^4$ .................... C07C 101/18; A61K 31/22
[52] U.S. Cl. ..................................... 514/547; 560/170
[58] Field of Search ......................... 560/170; 514/547

[56] References Cited

U.S. PATENT DOCUMENTS

| 4,439,438 | 3/1984 | Cavazza | 560/170 |
| 4,443,475 | 4/1984 | Cavazza | 560/170 |
| 4,551,477 | 11/1985 | Cavazza | 560/170 |

FOREIGN PATENT DOCUMENTS

| 37-5174 | 6/1962 | Japan | 560/170 |
| 754873 | 8/1956 | United Kingdom | 560/170 |
| 2077258 | 12/1981 | United Kingdom | 560/170 |

OTHER PUBLICATIONS

Wagner, "Synthetic Organic Chemistry," pp. 479–482, (1953).
Comber, Org. Prep. Proced. Int., 17, pp. 175–181, (1985).
McOmie, "Protective Groups in Organic Chemistry," pp. 183–185 & 192–196, (1973).

Primary Examiner—Michael L. Shippen
Attorney, Agent, or Firm—Bruce M. Collins

[57] ABSTRACT

Carnitine acetyl carnitate dichloride, a precursor of carnitine and acetyl carnitine, is prepared by condensing noncarnitine tert-butyl ester with the acid chloride of acetyl carnitine chloride and methylating the product of the condensation with methyl iodide, thereby obtaining acetyl carnitate of carnitine chloride iodide. This product is hydrolized with trifluoroacetic acid, thereby eliminating the tert-butyl ester. The so-obtained acetyl carnitate of carnitine chloride iodide is converted into the desired compound by eluting a solution of the chloride iodide on a strongly basic ion-exchange resin activated in Cl$^-$ form.

4 Claims, No Drawings

ESTER OF ACETYL CARNITINE, PROCESSES FOR ITS PREPARATION AND PHARMACEUTICAL COMPOSITIONS CONTAINING IT

The present invention relates to the novel compound carnitine acetyl carnitate dichloride, to processes for its preparation and to pharmaceutical preparations containing it as the active ingredient.

Although it has been found that carnitine acetyl carnitate behaves, from the point of view of its therapeutical effectiveness, substantially as a precursor of carnitine and acetylcarnitine, the possibility of synthetizing such compound is surprising since it has been positively ascertained that the species carnitine carnitate (or "bicarnesine") which, in the 1950's, some author believed that they had prepared and isolated as an independent molecular species actually does not exist. It is interesting to note, in this connection, that the very same authors who erroneously believed that they had synthesized the carnitate of carnitine (Binon and Deltour), proved that what they had believed to be a distinguished molecular species, derived from the condensation of two carnitine molecules was, in fact, only a substantially equimolecular mixture of carnitine and crotonoil betaine.

As mentioned, the acetyl carnitate of carnitine acts as a precursor of carnitine and of acetyl carnitine.

As to the therapeutic uses of L-carnitine, its activity is known, e.g., in the treatment of myopathies and of muscular dystrophies. L-carnitine is used in the field of cardiovascular diseases for the treatment of acute and chronic myocardial ischemia, of angina pectoris, of cardiac insufficiency and arrhythmia (U.S. Pat. Nos. 3,830,931 and 3,968,241). In the field of nephrology, L-carnitine is administered to chronic uraemic patients who undergo regular hemodialysis, for combating muscular asthenia and the arising of muscular cramps (U.S. Pat. No. 4,272,549). Other therapeutic uses relate to the normalization of the rate HDL/LDL+VLDL (U.S. Pat. No. 4,255,449) and the total parenteral nutrition (U.S. Pat. No. 4,254,147).

More recently, the utility of carnitine for improving the biochemical and behavioural parameters which are typical of senile age has been proved (Italian patent application No. 49398 A/82).

As to the therapeutic uses of acetylcarnitine known in the art, for example U.S. Pat. No. 4,194,006 describes the use of acetyl-carnitine for the therapeutic treatment of myocardial ischemia and arrhythmia. U.S. Pat. No. 4,343,816 describes the use of acetyl carnitine for the treatment of peripheral functional vasculopathy of the arteries, e.g., Raynaud's disease and acrocyanosis.

U.S. Pat. No. 4,346,107 discloses the therapeutic utility of acetyl carnitine in the treatment of patients suffering from altered cerebral metabolism as occurs, for instance, in senile and pre-senile dementia and in Alzheimers' disease. U.S. Pat. No. 4,415,589 describes its use as immunomodulator. U.S. Pat. No. 4,415,589 describes its therapeutic use in the treatment of vein's pathology, for example in venous stasis. Italian patent application No. 49644 A/82 describes its use in the therapeutic treatment of acquired (e.g., toxic or reulting from immobilization) and congenital (e.g., muscular dystrophy of Duchenne) muscular myopathy and dystrophy, where acetyl carnitine is surprisingly effective even in cases where carnitine does not attain its therapeutic goal.

The special usefulness of carnitine acetyl carnitate is evident in situations in which the activity of carnitine is intended to "complete" that of the acetyl carnitine, or whenever the directions of the one "border" on those of the other.

Examples of application are the treatment of muscular myopathy and dystrophy, the improvement of the biochemical and behavioural parameters of the senile age and the treatment of senile and presenile dementia.

Although the daily dosage to be administered depends, according to the judgement of the attending physician, on the weight, age and and general conditions of the ageing patient, it has been found that it is generally appropriate to administer from about 10 to about 30 mg/kg of body weight/day of carnitine acetyl carnitate.

Carnitine acetyl carnitate is formulated with the customary excipients employed for the preparation of compositions for oral or parenteral administration.

It has further been found that a pharmaceutical composition which is particularly suitable for the aforementioned therapeutic uses, comprises, when in unit dosage form, from about 500 to about 1000 mg of acetyl carnitate of carnitine.

According to the present invention, carnitine acetyl carnitate dichloride can be prepared according to two separate synthesis paths, illustrated in the following reaction schemes A and B:

SCHEME A

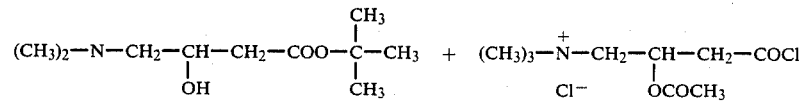

SCHEME A

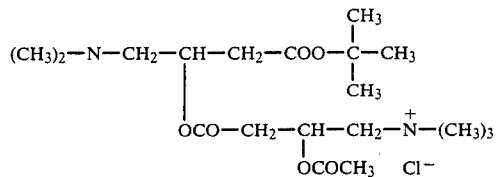

(III) ↓

$$(CH_3)_3 \overset{+}{-}N-CH_2-CH-CH_2-COO-\underset{CH_3}{\overset{CH_3}{\underset{|}{\overset{|}{C}}}}-CH_3$$
$$I^- \quad \underset{OCOCH_3 \quad Cl^-}{OCO-CH_2-CH-CH_2-\overset{+}{N}-(CH_3)_3}$$

(IV) ↓

$$(CH_3)_3\overset{+}{-}N-CH_2-CH-CH_2-COOH$$
$$Cl^- \quad \underset{OCOCH_3 \quad Cl^-}{OCO-CH_2-CH-CH_2-\overset{+}{N}-(CH_3)_3}$$

(V)

SCHEME B

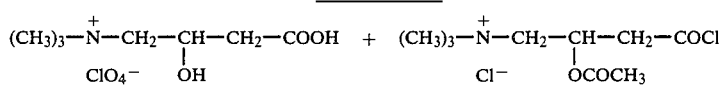

(VI) ↓ (II)

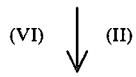
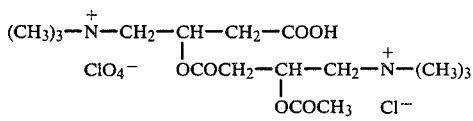

(VII) ↓

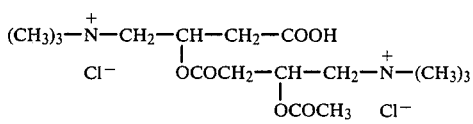

(V)

According to the process illustrated in scheme A, nor-carnitine tert-butylester (I) is reacted in an anhydrous inert organic solvent, for example methylene chloride, chloroform or acetonitrile, with the acid chloride of acetyl carnitine chloride (II), prepared according to techniques known in the art, in a molar ratio of between 1:1 and 1:1.5. The reaction mixture is kept under stirring for a period of between 8 to 24 hours. The temperature is maintained at about 10°–30° C.

The intermediate (III) obtained by concentrating the reaction solution is employed as such in the subsequent reaction.

Acetyl carnitate of carnitine tert-butyl ester chloride (III) is treated with methyl iodide in molar ratio 1:3–1:5 in methanol, and the solution is screened from light for about 24–48 hours.

The product (IV) is obtained by evaporating the solution. The said product is hydrolyzed with trifluoroacetic acid, for a period of time of about between 8 and 24 hours, at a temperature of about 20° and 35° C.

The addition of an organic solvent such as ethyl ether or dioxane causes the precipitation of acetyl carnitate of carnitine chloride iodide.

Acetyl carnitate of carnitine dichloride is obtained from the preceding precipitate by dissolving it in H$_2$O, eluting it on a strong basic resin of the Amberlite IRA 402 type, activated in Cl$^-$ form, and then by liophilizing or concentrating the aqueous solution obtained. According to the process illustrated in scheme B, carnitine perchlorate (VI) dissolved in acetonitrile is reacted with the acid chloride of acetyl carnitine chloride (II) dissolved in an anhydrous inert organic solvent, such as, for example CH$_2$Cl$_2$. Molar ratio (VI): (II)=1:1–1:1.5.

The reaction takes place under basic catalysis, preferably in the presence of an organic base such as pyridine or dimethyl aminopyridine. The reaction mixture is kept under stirring at a temperature of about between 10° and 35° C. for about 16–24 hours.

The product (VII) is isolated from the reaction mixture by concentrating it and is converted into compound (V) by eluting an aqueous solution of (VII) on strongly basic resin of the Amberlite IRA 402 type activated in Cl$^-$ form.

It will be apparent to the skilled person that the chloride anions of compound (V) may be substituted, by known processes, with other anions of pharmaceutically acceptable acids, such as acid aspartate, acid nitrate, acid phosphate, acid fumarate, lactate, acid maleate and acid sulfate.

EXAMPLE 1

(V) was prepared according to the process of scheme A.
(a) Preparation of acetyl carnitate of nor-carnitine tert-butyl ester chloride (III)

Nor-carnitine tert-butyl ester (2 g; 0.01 mol) was dissolved in anhydrous CH$_2$Cl$_2$ (25 cc) and to the resulting mixture there was added under stirring acid chloride of acetyl carnitine chloride (0.015 mol) diluted in anhydrous CH$_2$Cl$_2$.

The resulting solution was kept under stirring for 16 hours. Subsequently, the solution was filtered and concentrated to dryness under vacuum. The raw residue was utilized as such for the subsequent reaction.
(b) Preparation of acetyl carnitate of carnitine tert-butyl chloride iodide ester (IV)

Acetyl carnitate of nor-carnitine tert-butyl ester chloride (1 g; 0.0027 mol) was dissolved in 15 cc of anhydrous methanol. To the solution there was added CH$_3$I (1.4 g; 10 mmol). The mixture was kept for one night at room temperature and sheltered from light. The solvent was then evaporated under vacuum obtaining quantitative yields of (IV).
(c) Preparation of acetyl carnitate of carnitine dichloride (V).

Acetyl carnitate of carnitine tert-butyl ester chloride iodide (1 g; 0.002 mol) was dissolved in 5 cc of CF$_3$COOH and left at room temperature for 8 hours. To the reaction mixture there was added anhydrous ethyl ether, causing the precipitation of an oily product which was separated by decantation. The residue was dissolved in H$_2$O and eluted on IRA 402 resin activated in Cl$^-$ form. The eluted acid was liophilized, yielding 700 mg of acetyl carnitate of carnitine dichloride.

NMR D$_2$O δ 5,5

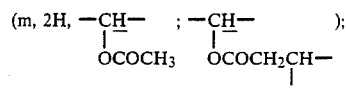

3,5 (m, 4H, 2(N$^+$—CH$_2$)); 3,1 (s, 19H, 2 (CH$_3$)$_3$N$^+$); 2,8–2,6 (m, 4H, —C$\underline{H}_2$COO—; —C$\underline{H}_2$COOH); 2,0 (s, 3H, —COCH$_3$).

EXAMPLE 2

(V) was prepared according to the process illustrated in scheme B.
(a) Preparation of carnitine perchlorate (VI)

Carnitine chloride (2 g; 0.01 mol) was suspended in anhydrous acetonitrile. To the suspension there was added silver perchlorate (2.5 g; 0.01 mol). The resulting mixture was kept under stirring in the dark for 1 hour. The silver chloride evolved was then removed by filtration and the filtrate was concentrated under vacuum. 2.5 g carnitine perchlorate were obtained.
(b) Preparation of acetyl carnitate of carnitine dichloride (V)

Carnitine perchlorate (1 g; 0.004 mol) was dissolved in 25 cc of anhydrous acetonitrile. To the solution there were added 0.1 cc anhydrous pyridine, and subsequently the acid chloride of acetyl carnitine chloride (1 g; 0.004 mol) diluted with anhydrous enthylene chloride. The solution was kept under stirring for about 16 hours. It was then filtered and then concentrated to dryness under vacuum thereby obtaining (VII).

(VII) was dissolved in H$_2$O and eluted on IRA 402 resin activated in Cl$^-$ form. The eluted acid obtained was lyophilized, thereby obtaining 1.5 g of acetyl carnitate of carnitine dichloride.

NMR showing as in Example 1.

I claim:
1. A compound of the formula:

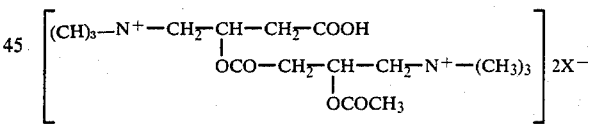

in which X is the anion of a pharmaceutically acceptable acid.

2. A compound according to claim 1 in which X$^-$ is the acid aspartate, acid citrate, acid phosphate, acid fumarate, lactate, acid maleate or acid sulfate anion.

3. The compound according to claim 1 wherein X$^-$ is the chloride anion.

4. A pharmaceutical composition in unit dosage form comprising from about 500 to about 1000 mg of a compound according to claim 3 in combination with a pharmaceutical carrier.

* * * * *